United States Patent [19]

Zeindler

[11] Patent Number: 5,213,097
[45] Date of Patent: May 25, 1993

[54] APPARATUS FOR THE TREATMENT OF DISEASES OF THE WALLS OF OPENINGS OR CAVITIES OF THE BODY

[75] Inventor: Kurt Zeindler, Ebikon, Switzerland
[73] Assignee: Zewa AG, Hergiswil, Switzerland
[21] Appl. No.: 911,373
[22] Filed: Jul. 13, 1992

Related U.S. Application Data

[63] Continuation of Ser. No. 599,820, Oct. 22, 1990, abandoned.

[30] Foreign Application Priority Data

Oct. 24, 1989 [CH] Switzerland .................. 3836/89

[51] Int. Cl.⁵ .................................................. A61F 7/12
[52] U.S. Cl. ................................. 128/401; 128/399; 128/786; 128/788; 606/27; 606/31; 606/32
[58] Field of Search ............ 128/399, 401, 24.1, 128/786, 788; 606/27, 28, 29, 30, 31, 32, 41, 42

[56] References Cited

U.S. PATENT DOCUMENTS

| | | | |
|---|---|---|---|
| 659,409 | 10/1900 | Mosher | 128/18 |
| 844,450 | 2/1907 | Harris | 604/41 |
| 1,690,926 | 11/1928 | Dequer | 128/401 |
| 1,964,732 | 7/1934 | Homan . | |
| 2,040,420 | 5/1936 | Wolff et al. | 128/401 |
| 2,078,686 | 4/1937 | Rowe | 128/401 |
| 2,777,445 | 1/1957 | Hart | 128/401 |
| 3,800,800 | 4/1974 | Garbe et al. | 128/788 |
| 4,142,529 | 3/1979 | Latenser, et al. | 128/401 |
| 4,227,535 | 10/1980 | Connor | 128/401 |
| 4,955,377 | 9/1990 | Lennox et al. | 128/401 |
| 5,007,437 | 4/1991 | Sterzer | 128/401 |

FOREIGN PATENT DOCUMENTS

| 618875 | 8/1980 | Switzerland . | |
| 0738596 | 6/1980 | U.S.S.R. | 128/401 |
| 1372668 | 7/1989 | U.S.S.R. | 128/401 |

Primary Examiner—Jessica J. Harrison
Attorney, Agent, or Firm—Nies, Kurz, Bergert & Tamburro

[57] ABSTRACT

A treatment apparatus including a probe to be inserted into openings and cavities of the body, a control apparatus having a battery which is chargeable by the public power network. A control current circuit includes an intermittent current impulse circuit which causes the heating unit of the probe to emit heat in form of intermittent heat impulses of adjustable magnitude. The apparatus finds application in the therapeutic treatment of diseases in the walls (tissue) of cavities of the body such as, e.g., hemorrhoides, and prostate conditions.

10 Claims, 3 Drawing Sheets

APPARATUS FOR THE TREATMENT OF DISEASES OF THE WALLS OF OPENINGS OR CAVITIES OF THE BODY

This application is a continuation of application Ser. No. 07/599,820, filed Oct. 22, 1990, now abandoned.

BACKGROUND OF THE INVENTION

1. Field of the Invention

The present invention relates to an apparatus for the treatment of diseases of the walls of openings of a human or a animal body, specifically of the walls of the terminal tract of the bowels or of the ureter, including a probe adopted to be inserted into a respective opening of the body, which probe has an electrical heating unit adapted to deliver heat to the wall of the opening of the body via a wall of the probe, and including further a control apparatus which contains a source of electrical energy, or is connectable to such source, such to transfer electrical energy to said heating unit of said probe.

2. Description of the Prior Art

Such apparatuses are generally known and available on the market. They have been developed specifically for the heat treatment of hemorrhoides and are used by the physician in his private practice, in clinics and hospitals, as well and also for domestic therapy. The apparatuses have proven themselves, and clinical tests revealed that they promote the circulation of the blood in the area of the anus and therewith reduce the size of the hemorrhoides, and this without the additional application of medicines. The tests revealed further that a therapeutics, is sensed by the patient as relatively pleasant.

Apart from the probe proper the known apparatuses consist of a control and regulating apparatus, which among others comprises a temperature display, a clock with display (actual time and a countdown timer) and the necessary switches, e.g. Start/Stop/Pause. The apparatus includes a control circuit which supplies and controls the probe during the treatment. Suitable circuits can be produced by any person skilled in the art of electrical engineering or electronics. The desired temperature is adjustable to a value of, e.g., in the range of 37°–46° C., whereby the circuit takes care of maintaining a maximal set temperature (the probe is provided with a corresponding temperature sensor). The apparatus is equipped with all necessary safety-systems.

Thus, the apparatus must be charged, e.g., by a built-in battery charger from the power supply network. The apparatus can not be put into operation as long as it is connected to the network. During the actual treating the apparatus is supplied by the built-in batteries and produces the desired heat in the probe.

The design of such a treatment apparatus is disclosed, e.g., in the Swiss Patent Specification CH-PS 618 875. Furthermore, the effects and the application of such an apparatus is described together with clinical results in the periodical "Schweizerische Rundschau fur Medizin (Praxis) 76, nr. 49" of the year 1987.

Although it has been possible to obtain satisfactory results by the known apparatuses, a search was made for possibilities to improve the effects of the treatment and at the same time to apply such to the treatment of diseases of the walls of other openings of the body, specifically of the walls of the prostate.

Tests have revealed that the effects can be improved considerably by intermittent heat impulses.

SUMMARY OF THE INVENTION

It is, therefore, a general object of the present invention to provide an apparatus for the treatment of diseases of the walls of openings of a human or animal body which produces improved effects of the therapy.

A further object is to provide an apparatus which produces intermittent heat impulses for the therapy.

Yet a further object is to provide an apparatus comprising a control circuit for the heating unit, which control circuit includes means for supplying the heating unit such with electrical current that later emits the heat in the form of intermittent heat impulses of an adjustable magnitude.

Still a further object is to provide an apparatus in which the means for supplying the heating unit with electrical current arranged in the control circuit comprise circuitry adapted to at least reduce the supply of current to the heating unit periodically for a predetermined time span in order to emit the heat in form of heat impulses.

A further object is to provide an apparatus in which the control circuit for the heating unit comprises further means for controlling the temperature generated by the heating unit and comprises additionally means for limiting the temperature, which limiting means are controlled by the controlling means.

Yet a further object is to provide a apparatus in which the electrical heating unit is an electrical resistance heater.

Still a further object is to provide an apparatus which comprises a sensor to detect and preferably control the temperature of the wall of the probe which transmits the heat generated towards the outside.

A further object is to provide an apparatus which is adjustable for the treatment of diseases of the walls of openings of the body having small diameters, e.g., for the treatment of diseases of the prostate.

Yet a further object is to provide an apparatus for the treatment of diseases of small diameter openings of the body in which the probe has the shape of a cylindrical body having a small diameter, in which the probe comprises further a balloon catheter by means of which after a inflating thereof the probe is insertable into a opening of a body having a small width, e.g., into a urethra or ureter. Such a procedure allows precise locating of the probe within the body.

A further object is to provide a apparatus which comprises a plurality of probes, e.g. of various shapes and diameters, which are selectively connectable to the control apparatus.

Still a further object is to provide an apparatus wherein for the treatment of diseases of the bowels the cylindrical shape of the probe without catheter includes at least one collar-like projecting abutment portion for preventing an uncontrolled sliding inwards of the probe.

A further object is to provide an apparatus wherein for the treatment of diseases of the ureter the probe has a small diameter and a cylindrical shape.

Yet a further object is to provide an apparatus in which the probe has the shape of an elongate body of which the center wall portion is adapted to transmit heat towards the outside and where at both sides of this center wall portion one electrically conducting wall portion is located, which two latter wall portions are electrically separated from each other and are connectable to differing electrical potentials, whereby in operation a potential difference is present over the contacting wall of the body.

A further object of the invention encompassing the improvement of the effects of the therapy by such apparatus is to provide the probe as an elongate body of which the center wall portion is adapted to transmit heat towards the outside and in which at both sides of this wall portion one electrically conducting wall portion is located, which two latter wall portions are electrically separated from each other and are connectable to differing electrical potentials, whereby in operation a potential difference is present over the contacting wall of the body.

Still a further object is to provide an apparatus in which the center wall portion of the probe consists of an electrically nonconductive material and wherein both sides of the adjacently located wall portions consist of an electrically conductive material.

BRIEF DESCRIPTION OF THE DRAWINGS

The invention will be better understood and objects other than those set forth above, will become apparent when consideration is given to the following description thereof. Such description makes reference to the annexed drawings wherein.

DESCRIPTION OF THE PREFERRED EMBODIMENTS

Figure 1:
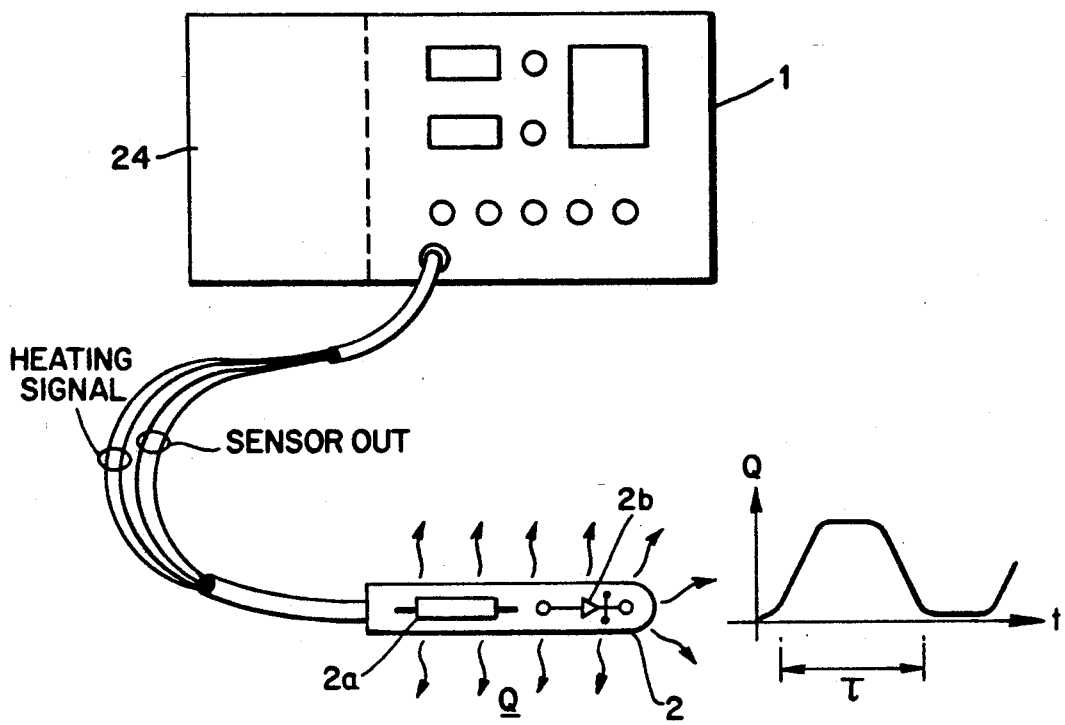
FIG. 1 is a schematic illustration of the entire apparatus structured in accordance with the present invention.

FIG. 1 of the drawing illustrates schematically a embodiment of the apparatus according to the invention such as used, e.g., for the heat treatment of hemorrhoides or with a correspondingly designed probe, and possibly together with a balloon catheter for heat treatment of the prostate.

The apparatus comprises a control apparatus 1 which contains the entire electric and electronic control circuit and includes various displays for information, such as a display of temperature, time, a countdown timer and the necessary switches and control knobs as well. Adjustable, among other variables is the maximal treatment temperature (adjustable, e.g. between 37°–50° C.), the time $\tau$ of the intermittent heat impulses Q, and the desired treatment time (e.g., 20–30 Minutes).

The control apparatus 1 includes also a battery charger, which if needed is connectable to the public power network, and one or a plurality of chargeable storage batteries.

Finally, the probe 2 which is to be inserted into the opening in the body to be treated is provided with the requisite power supply. The probe 2 contains an electrical heating device 2a and also a sensor 2b which serves for controlling the desired maximal temperature.

Figure 2:
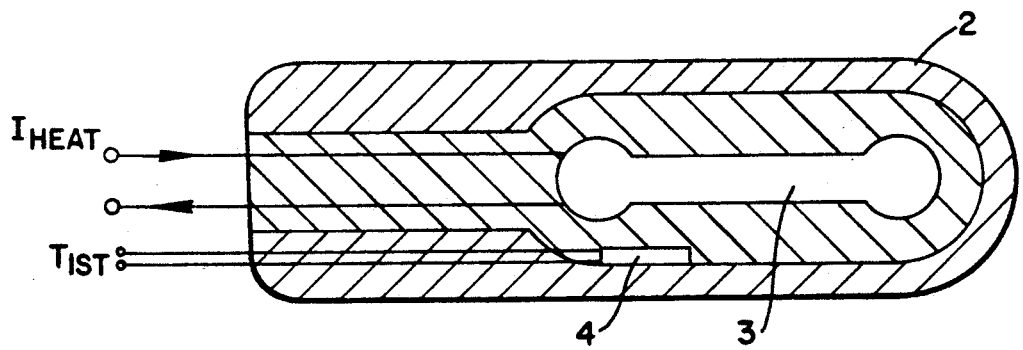
FIG. 2 is a schematic view of a longitudinal section through a probe.

FIG. 2 illustrates purely schematically such a probe 2 including a heating device in the form of a heating resistor element 3 and a sensor 4. The illustration indicates the shape of the probe 2 as a catheter-ureter probe.

The feed lines for the heating resistor element 3 and for the sensor 4 are preferably collected at the exit of the probe into a cable which is connectable to the control apparatus (see FIG. 1). Due to safety reasons (regulations) the connections to the apparatus are designed in a generally known manner such that when the apparatus is connected to the public power network it is not possible at the same time to connect the probe to this apparatus.

Figure 1A:
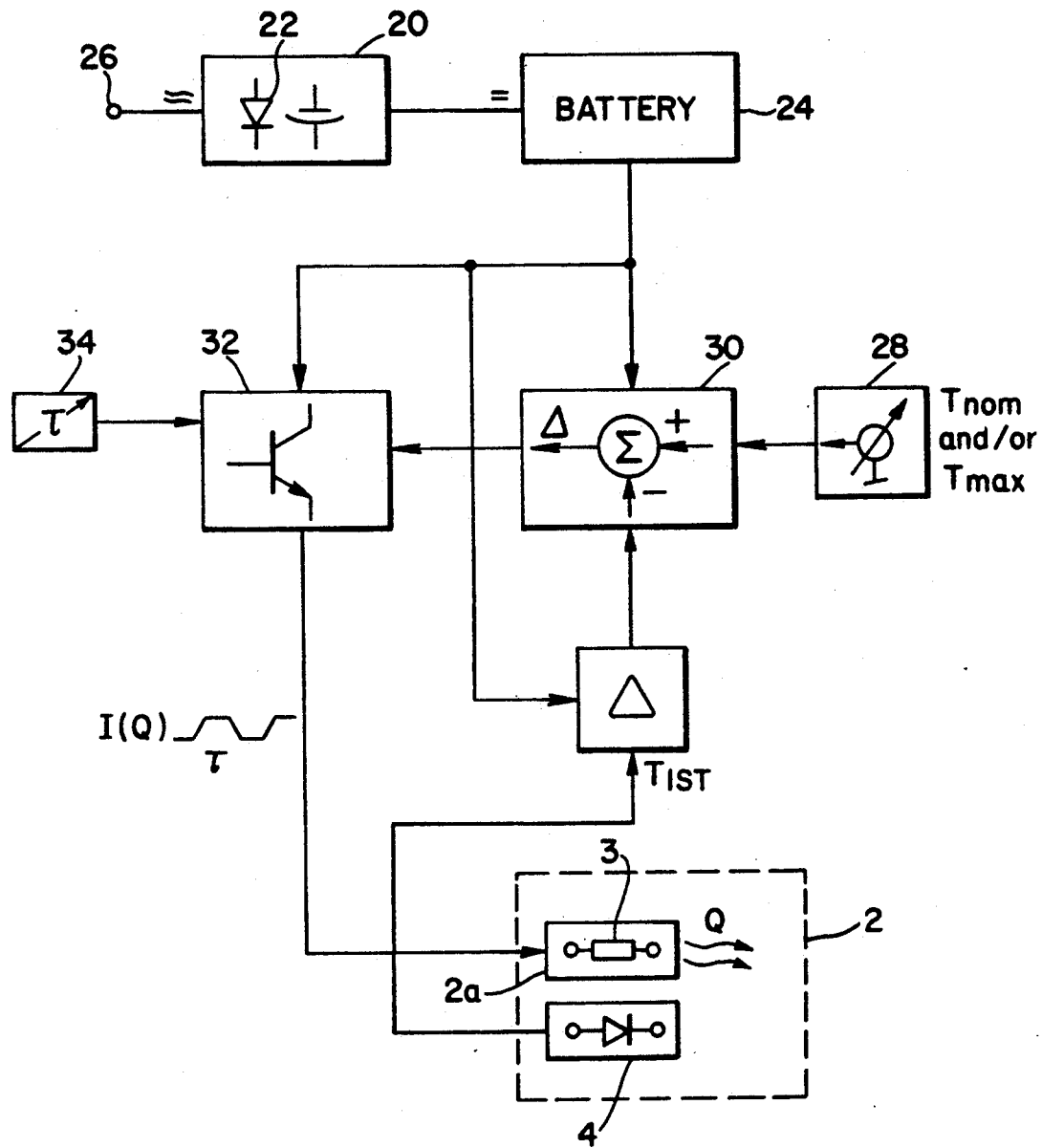
FIG. 1a is a schematic illustration of an electronic circuit in accordance with the present invention.

The control circuit is shown in FIG. 1a and includes a battery charger 20 including a rectifier 22 to provide a DC output to battery 24 from an AC source 26. A temperature input control 28 permits a selected temperature to be input to comparator 30, which receives an actual temperature signal from temperature sensor 4 and provides a difference signal to control circuit 32. A timer 34 is connected with control circuit 32 to periodically reduce the supply of current from control circuit 32 to provide current pulses 36 to heating unit 3. Means are arranged in the control circuit for the heating unit, see diagram of FIG. 1a, which are operative to reduce the power supply to the heating unit intermittently, during a predetermined time, e.g., periodically such that the heating unit delivers the heat Q produced in the unit in the form of intermittent heat impulses, whereby the maximal temperature Tma of the heat impulses is adjustable.

Figure 3:
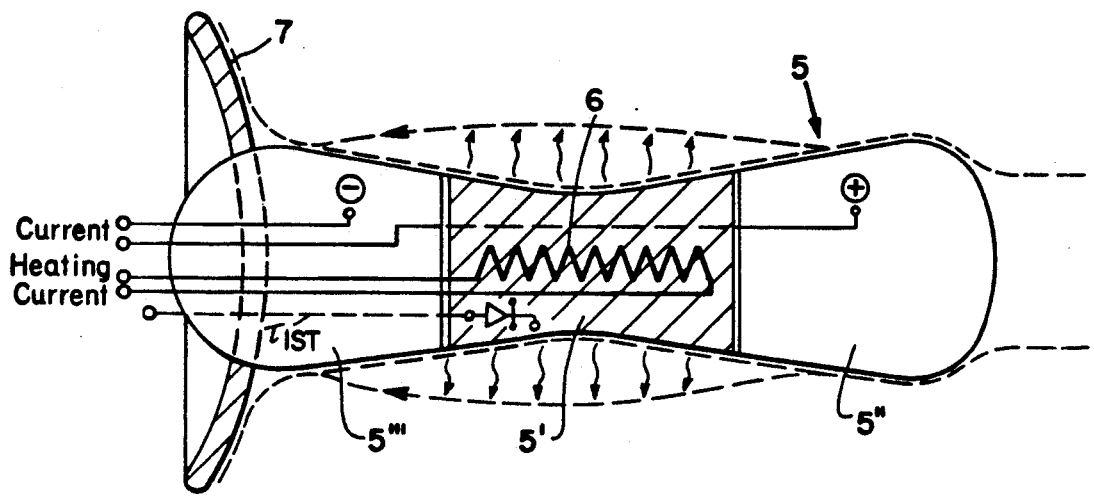
FIG. 3 is a schematic view of a further embodiment of the probe, including a center heating portion and two end portions which are connectable to two differing potentials, here for application for the bowels.

FIG. 3 of the drawing illustrates a variant of a probe 5 for a bowels application. It consists of an elongate, pin-like base body through the center wall portion 5', from which heat is emitted toward the outside of the probe by means of the electrical heating unit (continuously, or preferably in the form of intermittent heat impulses) The two wall portions 5'' and 5''' located at both sides adjacent the center wall portion 5' are electrically insulated from the center wall portion and are connected to differing potentials + and −, resp., such that in operation a current can flow through the tissue via the (moist) wall of the body, which leads to a further improvement of the effects of the therapy. The power supply to the wall portions 5'', 5''' can proceed continuously or also intermittently. In the latter case the power supply can occur in synchronism with the power supply to the heating resistor element 6. Preferably, the probe 5 includes at one end a flange-like abutment 7 in order to prevent the probe from penetrating too far into the opening of the body.

Figure 4:
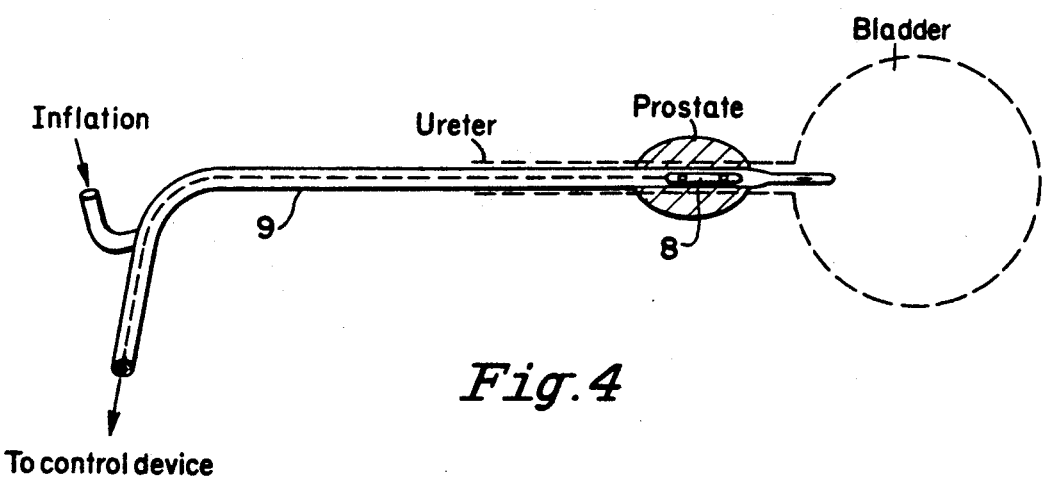
FIG. 4 is a schematic illustration of an apparatus consisting of a balloon catheter and a probe.

FIG. 4., finally, illustrates an apparatus in accordance with the invention (without control apparatus), which includes outside of the very compact probe 8 a s called balloon catheter 9. This allows insertion of the probe 8 into relatively narrow openings or cavities of the body, and to locate the probe there precisely, such as, e.g., in ureters, in order to therewith treat diseases of the prostate. The operational functioning of the balloon catheter is generally known to persons skilled in the art.

While there are shown and described present preferred embodiments of the invention, it is to be distinctly understood that the invention is not limited thereto, but may be otherwise variously embodied and practiced within the scope of the following claims.

I claim:

1. An apparatus for the treatment of diseases of the walls of a human or an animal body, the apparatus comprising: a probe for insertion into a respective opening of the body, which probe has an electrical heating unit for delivering heat to the wall of the opening of the body via a wall of the probe, and a control apparatus coupled with a source of electrical energy and with the electrical heating unit to transfer electrical energy from the source of electrical energy to said heating unit of said probe, the control apparatus including a control circuit for said heating unit and including a temperature limit control for setting the maximum temperature of the heating unit, which control circuit includes an intermittent current impulse circuit coupled with the source of electrical energy for supplying said heating unit with intermittent electrical current pulses so that the heating unit emits heat in the form of intermittent heat impulses, wherein the intermittent current impulse circuit includes a manually operable, variable timer for manually setting the time duration of the individual intermittent heat impulses.

2. The apparatus of claim 1, in which said control circuit for said heating unit includes control means for controlling the temperature generated by said heating unit and also includes temperature limiting means for limiting said heating unit temperature, which temperature limiting means are controlled by said control means.

3. The apparatus of claim 1, in which said electrical heating unit is an electrical resistance heater.

4. The apparatus of claim 1, including a temperature sensor for detecting the temperature of the wall of said probe.

5. The apparatus of claim 1, wherein said probe has the shape of a cylindrical body having a small diameter, in which said probe includes an external balloon catheter by means of which after inflation of the catheter within a body opening said probe is insertable through the catheter into the opening and at a desired position within the body.

6. The apparatus of claim 1, comprising a plurality of exchangeable probes which are selectively connectable to said control apparatus.

7. The apparatus of claim 1, in which said probe has the shape of an elongate body of which a center wall portion is adapted to transmit heat towards an outer surface of the probe, and wherein at each longitudinal end of said center wall portion an electrically conducting wall portion is located, which two electrically conducting wall portions are electrically separated from each other and include connection means that are connectable to differing electrical potentials, whereby in operation a potential difference is present over the outer surface of the probe.

8. An apparatus for the treatment of diseases of the walls of openings of a human or an animal body, comprising: a probe for insertion into a respective opening of the body, which probe includes an electrical heating unit for delivering heat to the wall of the opening of the body via an outer wall of the probe, including connection means for connecting the heating unit with a control apparatus for controlling the supply of electrical energy to the heating unit, in which said probe is in the form of an elongate body having a central annular wall portion and outer end annular wall portions, wherein the outer end wall portions are separated from each other by the central wall portion and are positioned at opposite ends of the central wall portion of the probe, and wherein the central wall portion is adapted to receive and to transmit to the wall of the opening of the body heat emitted by the electrical heating unit, wherein at longitudinal ends of said central wall portion a respective one of the outer end wall portions is located and which is electrically separated from the other end wall portion, which end wall portions each include respective connection means that are connectable to differing electrical potentials, whereby in operation a potential difference is present between the outer end wall portions of the probe to cause a current to flow through body tissue defining the wall of the opening of the body.

9. The apparatus of claim 8, in which said center wall portion is formed from an electrically nonconductive material and the two end wall portions are formed from an electrically conductive material.

10. The apparatus of claim 8, in which a flange-like radially projecting abutment is located at one end of said elongate probe body.

* * * * *